United States Patent
Huang et al.

[11] Patent Number: 6,002,962
[45] Date of Patent: Dec. 14, 1999

[54] IMPLANTABLE TRIPHASIC WAVEFORM DEFIBRILLATOR

[75] Inventors: Jian Huang, Birmingham, Ala.; Bruce H. KenKnight, Maple Grove, Minn.; Raymond E. Ideker, Birmingham, Ala.

[73] Assignee: UAB Research Foundation, Birmingham, Ala.

[21] Appl. No.: 09/059,819

[22] Filed: Apr. 14, 1998

Related U.S. Application Data

[60] Provisional application No. 60/043,509, Apr. 14, 1997.

[51] Int. Cl.[6] .................................................. A61N 1/39
[52] U.S. Cl. .................................................. 607/5; 607/7
[58] Field of Search .................................... 607/5, 7

[56] References Cited

U.S. PATENT DOCUMENTS

| | | |
|---|---|---|
| 4,637,397 | 1/1987 | Jones et al. |
| 4,800,883 | 1/1989 | Winstrom . |
| 4,821,723 | 4/1989 | Baker, Jr. et al. |
| 4,850,357 | 7/1989 | Bach, Jr. . |
| 5,107,834 | 4/1992 | Ideker et al. |
| 5,184,616 | 2/1993 | Weiss . |
| 5,224,476 | 7/1993 | Ideker et al. ................... 607/9 |
| 5,431,682 | 7/1995 | Hedberg . |
| 5,522,853 | 6/1996 | Kroll . |
| 5,601,608 | 2/1997 | Mouchawar ................... 607/5 |

FOREIGN PATENT DOCUMENTS

| | | |
|---|---|---|
| 9623546 | 8/1996 | WIPO ............... A61N 1/39 |
| WO 96/23546 | 8/1996 | WIPO . |

OTHER PUBLICATIONS

Int'l Search Report; Int'l App'n No.:PCT/US 98/07487; Filed Apr. 14, 1998.

*Primary Examiner*—William E. Kamm
*Assistant Examiner*—Carl H. Layno
*Attorney, Agent, or Firm*—Myers Bigel Sibley & Sajovec

[57] ABSTRACT

An implantable system for the defibrillation or cardioversion of a patient's heart comprises a plurality of electrodes configured for delivering a defibrillation pulse along a predetermined current pathway in the heart. The plurality of electrodes includes a first electrode configured for positioning in the patient's heart. The system includes a power supply and a control circuit. The control circuit is operatively associated with the electrodes and the power supply.

12 Claims, 9 Drawing Sheets

IMPLANTABLE TRIPHASIC WAVEFORM DEFIBRILLATOR

This application claims benefit of Provisional Appl. No. 60/043,509, filed Apr. 14, 1997.

FIELD OF THE INVENTION

The present invention relates to implantable cardioverter/defibrillators in general, and particularly relates to implantable cardioverter/defibrillators that employ a triphasic waveform.

BACKGROUND OF THE INVENTION

Improving the effectiveness of defibrillation waveforms will allow the size of implantable cardioverter defibrillators to be reduced. Biphasic waveforms were a first step towards improving waveform effectiveness. However, for biphasic waveforms, the optimum strength of the second phase that minimizes the shock strength required for defibrillation is much larger than the optimum strength of the second phase that minimizes the amount of tissue damage caused by the defibrillation.

U.S. Pat. No. 4,637,397 to Jones and Jones, titled "Triphasic Wave Defibrillation", describes one effort to improve upon the biphasic waveform. This patent describes a method and apparatus for the stimulation of cells in arrhythmic myocardial tissues by administering, a triphasic waveform comprising, in sequence, a conditioning pulse, a defibrillating or correcting pulse of opposite polarity to the conditioning pulse, and then a healing pulse with the same polarity as the conditioning pulse. Jones does not suggest any particular implementation for their waveform. Rather, it is simply stated that means for applying the wave to fibrillating myocardial tissue "may comprise any convenient device conventionally used in practicing defibrillation techniques." (see Column 4 line 61 to Column 5 line 9 therein).

Unfortunately, the triphasic waveform suggested by Jones has not been successfully implemented. The problem is summarized in U.S. Pat. No. 5,522,853 to Kroll, which notes at column 2 lines 52–64 that: "the triphasic waveform suggested by Jones et al. has been shown to be no more effective than a traditional biphasic waveform. Manz, M. et al., Can Triphasic Shock Waveforms Improve ICD Therapy in Man? *Supplement to Circulation*, Vol. 88, No. 4, Part 2, Oct. 1993, Abst. 3193."

SUMMARY OF THE INVENTION

An implantable system for the defibrillation or cardioversion of the heart of a patient in need of such treatment is disclosed. The system comprises a plurality of electrodes configured for delivering a defibrillation pulse along a predetermined current pathway in the heart, the plurality of electrodes including a first electrode configured for positioning within the heart, and preferably within the right ventricle of the heart. The system includes a power supply and a control circuit, the control circuit operatively associated with the electrodes and the power supply. The control circuit is configured for delivering a triphasic defibrillation pulse through the electrodes, with the triphasic defibrillation pulse comprising a first phase, a second phase having a polarity opposite from said first phase, and a third phase having a polarity the same as said first phase. The control circuit is preferably configured so that the first electrode is an anode for the first and third phases of the triphasic defibrillation pulse.

A second aspect of the present invention is a system as given above implanted within said subject in the indicated configurations for carrying out the method described below.

A third aspect of the present invention is an implantable defibrillator configured for use in the system described above, and for carrying out the method described below.

A fourth aspect of the present invention is a method for the defibrillation or cardioversion of the heart of a patient in need of such treatment. The method comprises positioning a plurality of electrodes for delivering a defibrillation pulse along a predetermined current pathway in the heart, the plurality of electrodes including a first electrode positioned within the heart, and preferably within in the right ventricle of the heart, and then delivering a triphasic defibrillation pulse as described above through the electrodes. The first electrode is preferably an anode for the first phase and third phase of the triphasic defibrillation pulse.

The present invention is explained in greater detail in the drawings herein and the specification set forth below.

DETAILED DESCRIPTION OF THE INVENTION

The present invention may be used to treat all forms of cardiac tachyarrythmias, including ventricular fibrillation, with defibrillation (including cardioversion) shocks or pulses. The treatment of polymorphic ventricular tachycardia and ventricular fibrillation are particularly preferred.

Anatomically, the heart includes a fibrous skeleton, valves, the trunks of the aorta, the pulmonary artery, and the muscle masses of the cardiac chambers (i.e., right and left atria and right and left ventricles). The schematically illustrated portions of the heart 30 illustrated in FIG. 1 includes the right ventricle "RV" 32, the left ventricle "LV" 34, the right atrium "RA" 36, the left atrium "LA" 38, the superior vena cava "SVC" 48, the coronary sinus "CS" 42, the great cardiac vein 44, the left pulmonary artery 45, and the coronary sinus ostium or "os" 40.

The driving force for the flow of blood in the heart comes from the active contraction of the cardiac muscle. This contraction can be detected as an electrical signal. The cardiac contraction is triggered by electrical impulses traveling in a wave propagation pattern which begins at the cells of the SA node and the surrounding atrial myocardial fibers, and then traveling into the atria and subsequently passing through the AV node and, after a slight delay, into the ventricles.

The beginning of a cardiac cycle is initiated by a P wave, which is normally a small positive wave in the body surface electrocardiogram. The P wave induces depolarization of the atria of the heart. The P wave is followed by a cardiac cycle portion which is substantially constant with a time constant on the order of 120 milliseconds ("ms").

The "QRS complex" of the cardiac cycle occurs after the substantially constant portion. The dominating feature of the QRS complex is the R wave which is a rapid positive or negative deflection. The R wave generally has an amplitude greater than any other wave of the cardiac cycle, and has a spiked shape of relatively short duration with a sharp rise, a peak amplitude, and a sharp decline. The R wave is the depolarization of the ventricles and therefore, as used herein, the term "ventricle activations" denotes R waves of the cardiac cycle. The QRS complex is completed by the S wave, which is typically a small deflection that returns the cardiac signal to baseline. Following the S wave, the T wave occurs after a delay of about 250 ms. The T wave is relatively long in duration (e.g., about 150 ms). The cardiac cycle between the S wave and the T wave is commonly referred to as the ST segment. The T wave is a sensitive part of the cardiac cycle, during which an atrial defibrillation shock is to be avoided, in order to reduce the possibility of an induced (and often fatal) ventricular fibrillation. The next cardiac cycle begins with the next P wave. The typical duration of a complete cardiac cycle is on the order of about 800 ms.

Various embodiments of the present invention can be illustrated with reference to FIG. 1. The defibrillator 10 of FIG. 1 includes an implantable housing 13 that contains a power supply and a hermetically sealed electronic control circuit. The housing includes an electrode comprising an active external portion 16 of the housing, with the housing 13 preferably implanted in the left thoracic region of the patient (e.g., subcutaneously, in the left pectoral region) in accordance with known techniques as described in G. Bardy, U.S. Pat. No. 5,292,338. The system includes a catheter 20 which is insertable into the heart (typically through the superior or inferior vena cava) without the need for surgical incision into the heart. The term "catheter" as used herein includes "stylet" and is also used interchangeably with the term "lead". The catheter 20 contains electrode leads 20a, 20b, respectively.

Figure 1:
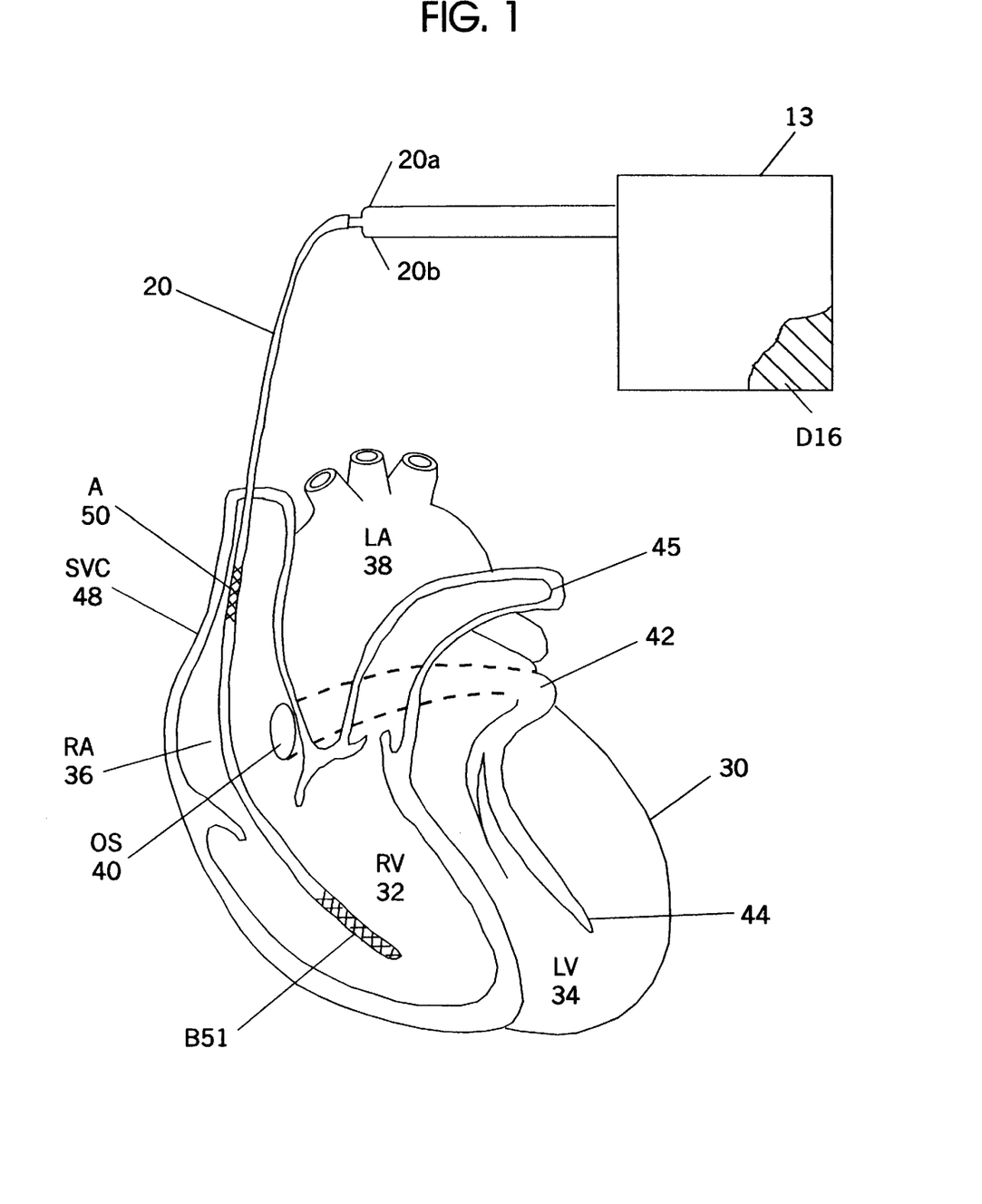
FIG. 1 is a schematic illustration of one embodiment of the present invention.

As illustrated in FIG. 1, the system includes an electrode A; 50 that resides in the superior vena cava or innominate vein, and an electrode B; 51 positioned in the right ventricle. The active external portion of the housing 16 serves as an electrode D.

Figure 2:
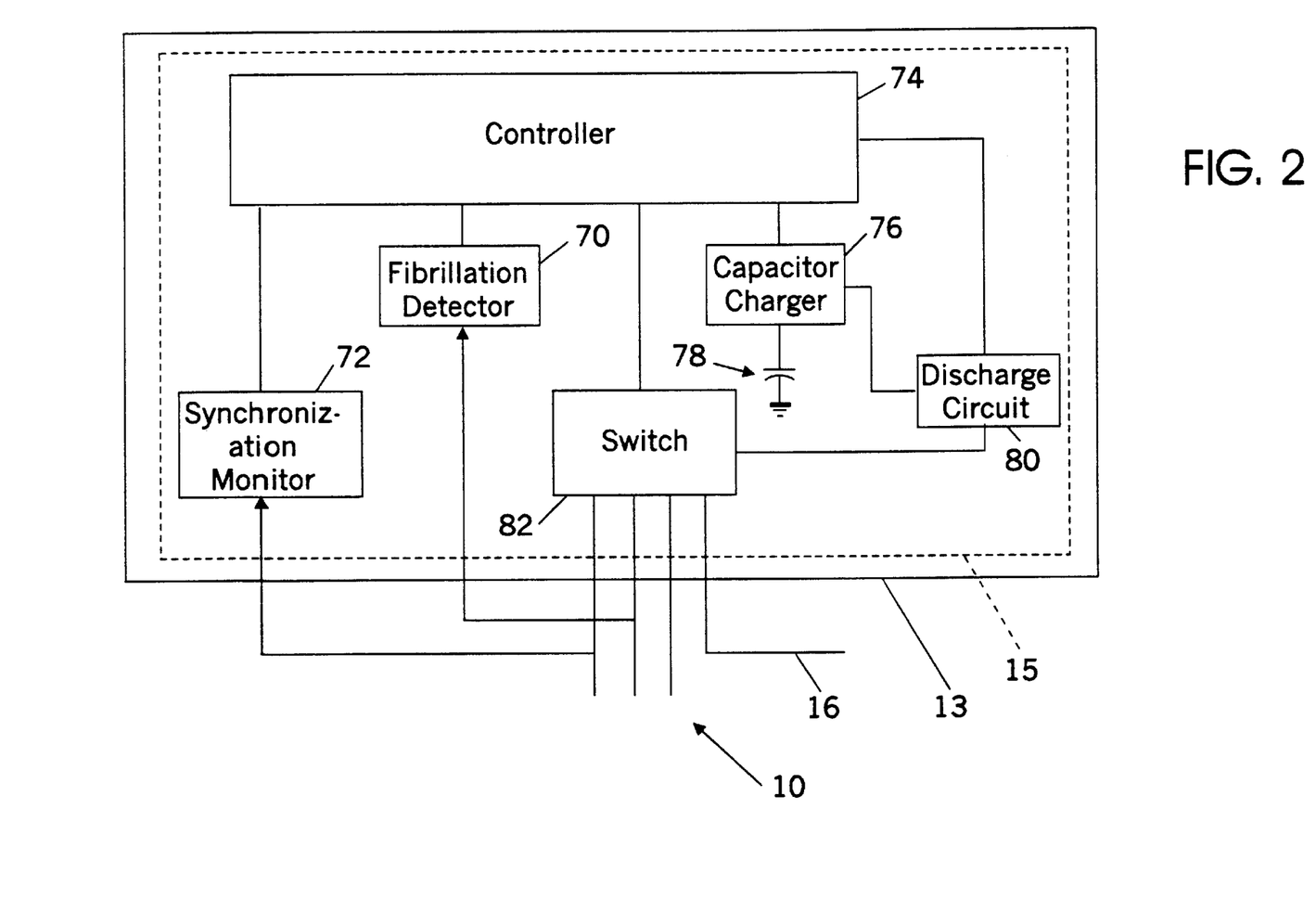
FIG. 2 schematically illustrates the control circuitry employed in an apparatus of the present invention.

FIG. 2 illustrates one example of an implantable housing 13 containing an electronic circuit 15, which includes one or more amplifiers (not shown) for amplifying sensed cardiac signals. The amplified signals are analyzed by an detector 70 which determines if ventricular fibrillation (or other arrythmia, depending on the specific treatment for which the device is configured) is present. The detector 70 may be one of several known to those skilled in the art. Although, as illustrated, a sensing signal is provided by the electrode A 50, it will be appreciated by those of skill in the art that the sensing electrode may also be a plurality of sensing electrodes with a plurality of signals, such as bipolar configurations, and may also be electrodes that are positioned in alternate cardiac areas as is known in the art, such as for example, the CS. In this situation, the input line to the detector may be a plurality of lines which if providing only sensing will provide an input to the detector.

The defibrillation electrodes may alternately be configured to sense cardiac cycles, or may have smaller sensing electrodes placed adjacent thereto and thereby provide input to the electronics package as well as provide a predetermined stimulation shock output to predetermined cardiac areas as directed by the controller.

The electronic circuit 15 also includes a cardiac cycle monitor ("synchronization monitor 72") for providing synchronization information to the controller 74. As discussed below, the synchronization is typically provided by sensing cardiac activity in the RV, but may also include other sensing electrodes which can be combined with the defibrillation electrodes or employed separately to provide additional assurance that defibrillation shock pulses are not delivered during sensitive portions of the cardiac cycle so as to reduce the possibility of inducing ventricular fibrillation.

Upon a signal from the detector 70, the controller 74, in turn, signals a capacitor charging circuit 76 which then charges the storage capacitor 78 to a predetermined voltage, typically from a battery source (not shown). The storage capacitor is typically 20 to 400 microfarads in size, and may be a single capacitor or a capacitor network (further, as discussed below, separate pulses can be driven by the same or different capacitors). The discharge of the capacitor is controlled by the controller 74 and/or a discharge circuit 80. The controller, based on information from the synchronization monitor 72, typically allows or directs the preselected shock pulse to be relayed to either a discharge circuit for further processing (i.e., to further shape the waveform signal, time the pulse, etc.) or directly to a switch. The controller may also control the proper selection of the predetermined defibrillation electrode pair(s), where multiple defibrillation electrodes are used, to direct the switch to electrically activate a desired electrode pair to align the predetermined electric shock pulse pathway through which the shock pulse is provided. As an alternative to a detector, the defibrillation pulses may be triggered by an external signal administered by a physician, with the physician monitoring the patient for the appropriate time of administration.

Numerous configurations of capacitor and control circuitry may be employed. The power supply may include a single capacitor, and the control circuit may be configured so that both the auxiliary pulse and the defibrillation pulse are generated by the discharge of the single capacitor. The power supply may include a first and second capacitor, with the control circuit configured so that the auxiliary pulse is generated by the discharge of the first capacitor and the defibrillation pulse is generated by the discharge of the second capacitor. In still another embodiment, the power supply includes a first and second capacitor, and the control circuit may be configured so that the auxiliary pulse is generated by the discharge (simultaneous or sequential) of both the first and second capacitors, and the defibrillation pulse likewise generated by the discharge of the first and second capacitors.

The active external portion 16 of the housing, which serves as an electrode, may be replaced with, supplemented with or coupled to one or more (e.g., three) subcutaneous electrodes, which may be implanted on the torso below the axilla and above the nipple.

Figure 3:
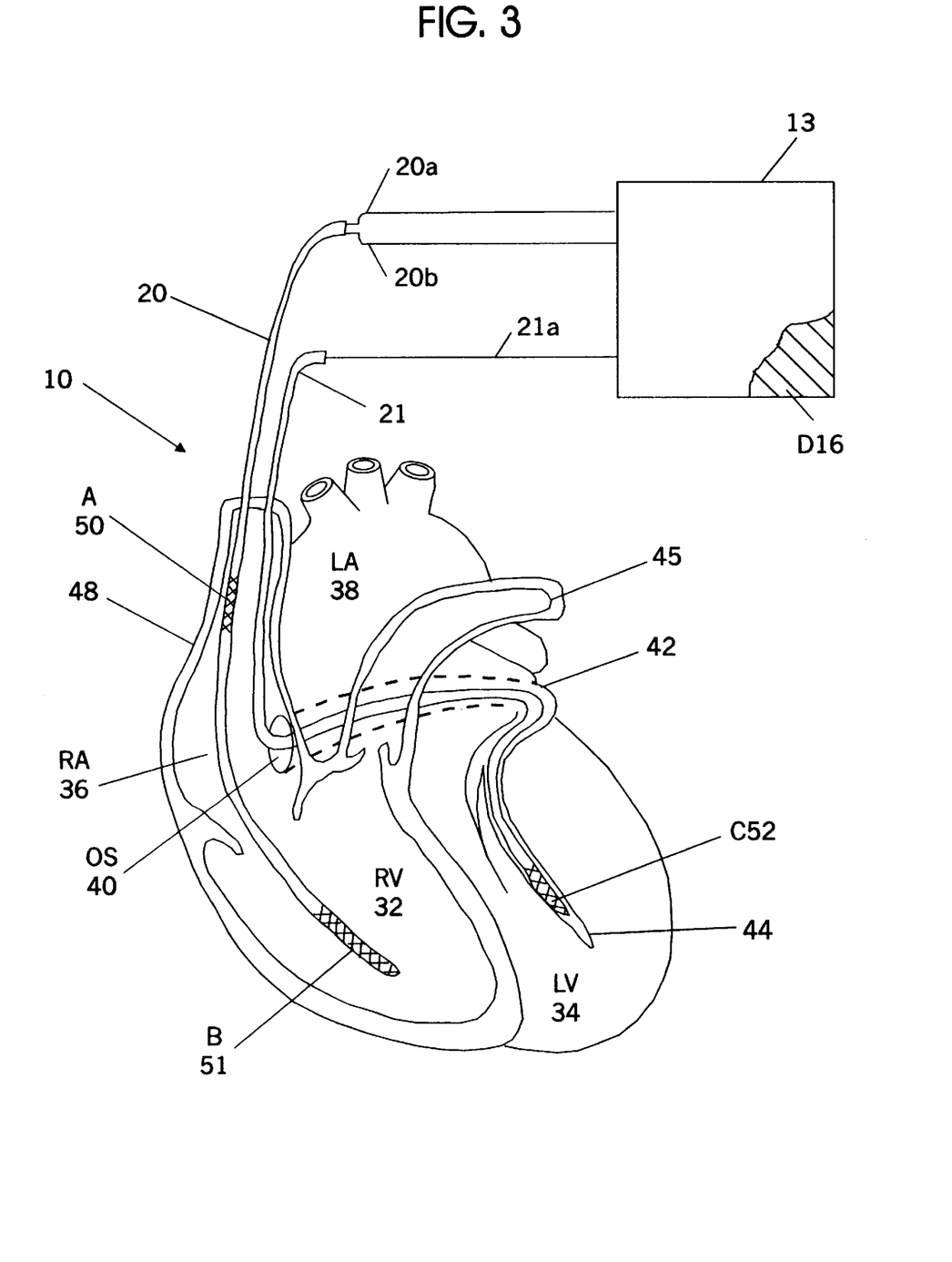
FIG. 3 is a schematic illustration of an alternate embodiment of the present invention.

FIG. 3 illustrates various additional electrode configurations that may be used to carry out the present invention. Various electrode configurations for the triphasic pulse, as delivered through the apparatus of FIG. 3, are given in Table 1 below:

TABLE 1 electrode pairings.

B + C → A + D
A → B
C → D
B → C
C → A

Electrodes may be of either polarity, and may be positioned on different leads or, where possible, on the same lead. Electrode pairings that include at least one electrode "B" in the right ventricle are preferred, and pairings that include at least one electrode "B" in the right ventricle as the anode for the first and third phases are particularly preferred.

In general, the first phase of the defibrillation pulse will be from 3 to 50, more preferably from 5 to 40, and most preferably from 10 to 15, milliseconds in duration. The second phase of the defibrillation pulse will be from 2 to 15, more preferably from 6 to 12, and most preferably from 8 to 10, milliseconds in duration. The third phase of the defibrillation pulse will be from one to 15, more preferably from 2 to 6, and most preferably from 3 to 5 milliseconds in duration.

The energy of the defibrillation pulse (including all three phases) will, in general, be from 2 or 5 to 25, 35, or 40 Joules.

As used herein, the term "tilt", when expressed as a percentage, for a phase or series of phases, is determined as:

$$\left(1 - \frac{\text{trailing edge voltage}}{\text{leading edge voltage}}\right) \times 100$$

for the phase or phases in question. For example, the tilt of the entire defibrillation is based on the leading edge voltage of the first phase and the trailing edge voltage of the last phase. A higher percentage tilt indicates a steeper or greater tilt for the phase or phase in question. The entire defibrillation waveform preferably has a tilt of at least 40 or 50 percent, and more preferably has a tilt of 75 to 90 percent.

The present invention is explained in greater detail in the following non-limiting examples.

EXAMPLE 1

Animal model preparation.

Animals were prepared in accordance with standard techniques. In brief, domestic farm swine were tranquilized via an intramuscular injection of ketamine (20–22 mg/kg) and acerpromazine (1.1 mg/kg). An endotracheal tube was inserted and the cuff was inflated to provide closed circuit ventilation. After about 10–15 minutes, anesthesia was induced with an intravenous bolus injection of sodium pentobarbital (10–20 mg/kg) through a 20 prominent ear vein. The animal was placed in dorsal recumbence and a deep surgical plane of anesthesia was maintained with continuous intravenous infusion of sodium pentobarbital (0.05 mg/kg/min).

Defibrillation electrode placement.

Electrode placement was carried out in accordance with standard techniques. In brief, defibrillation electrodes mounted on a commercially available lead system (ENDOTAK™ model 0094, CPI/Guidant Corp., St. Paul, Minn.) were introduced through a right jugular venotomy. The distal coil electrode (4.0 cm length) was advanced under fluoroscopic guidance to the right ventricular apex. The proximal coil (6.8 cm length) was positioned in the superior vena cava using fluoroscopic guidance. The distal and proximal catheter electrodes were used to deliver all shocks. An empty implantable defibrillator housing was implanted subcutaneously, with the center of the housing one centimeter below the left clavicle, to serve as the active "can" electrode.

Fibrillation.

Ventricular fibrillation was induced with 60 Hz alternating current (50–100 mA peak to peak) applied to the pacing tip electrode of endocardial lead positioned in the right ventricle. In all episodes, fibrillation was allowed to persist for 10±1 seconds prior to delivery of the defibrillation test shock. When the test failed to defibrillate, the heart was immediately defibrillated with a rescue shock given through the transvenous catheter lead system.

Defibrillation waveforms.

All shocks were delivered by the VENTAK™ external cardioverter defibrillator (model 2815, CPI/Guidant Corp., St Paul, Minn.), research modified, for capacitances of 300 $\mu$F or 140 $\mu$F.

Figure 4:
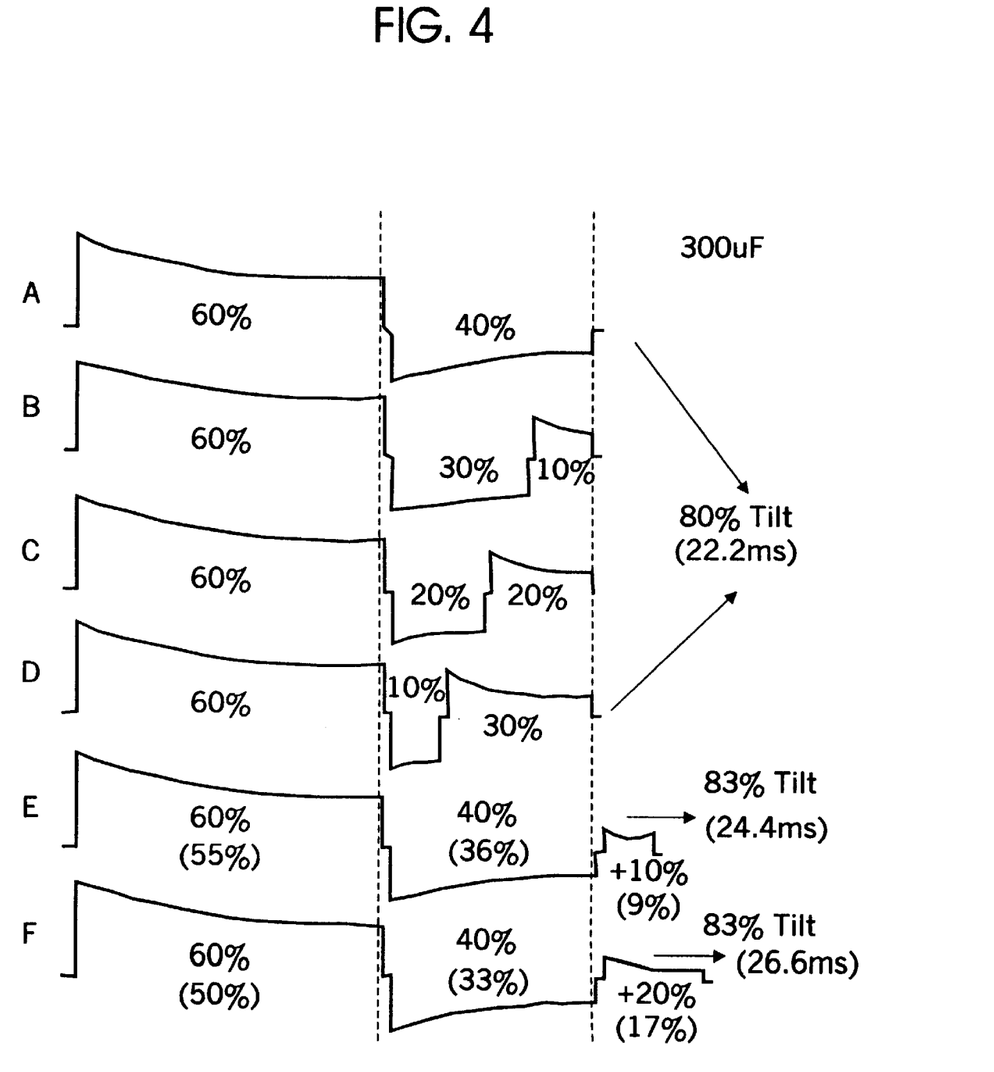
FIGS. 4A–4F illustrate various triphasic waveforms of the present invention, along with several biphasic waveforms.

Delivered biphasic and triphasic waveforms are schematically illustrated in FIG. 4. Percentages refer to the percent duration of each phase of the total duration of the waveform; the total duration of each waveform in milliseconds is given in brackets in the right column. Waveforms E and F give percentages for each phase that total 110% and 120%, respectively, with percentages for each phase that total 100% being given in parentheses. The tilt given is for the total waveform, from leading edge voltage of the first phase to trailing edge voltage of the last phase. Waveforms A to F were delivered with a 300 $\mu$F capacitor. Waveform A' was the same as waveform A except that it was delivered with a 140 $\mu$F capacitor. The following electrode polarities were tested for each waveform:

1. The RV electrode cathode to the SVC and shell electrode anode (RV->SVC+Can);
2. The SVC and shell electrode cathode to the RV electrode anode (SVC+Can->Rv+).

Figure 5:
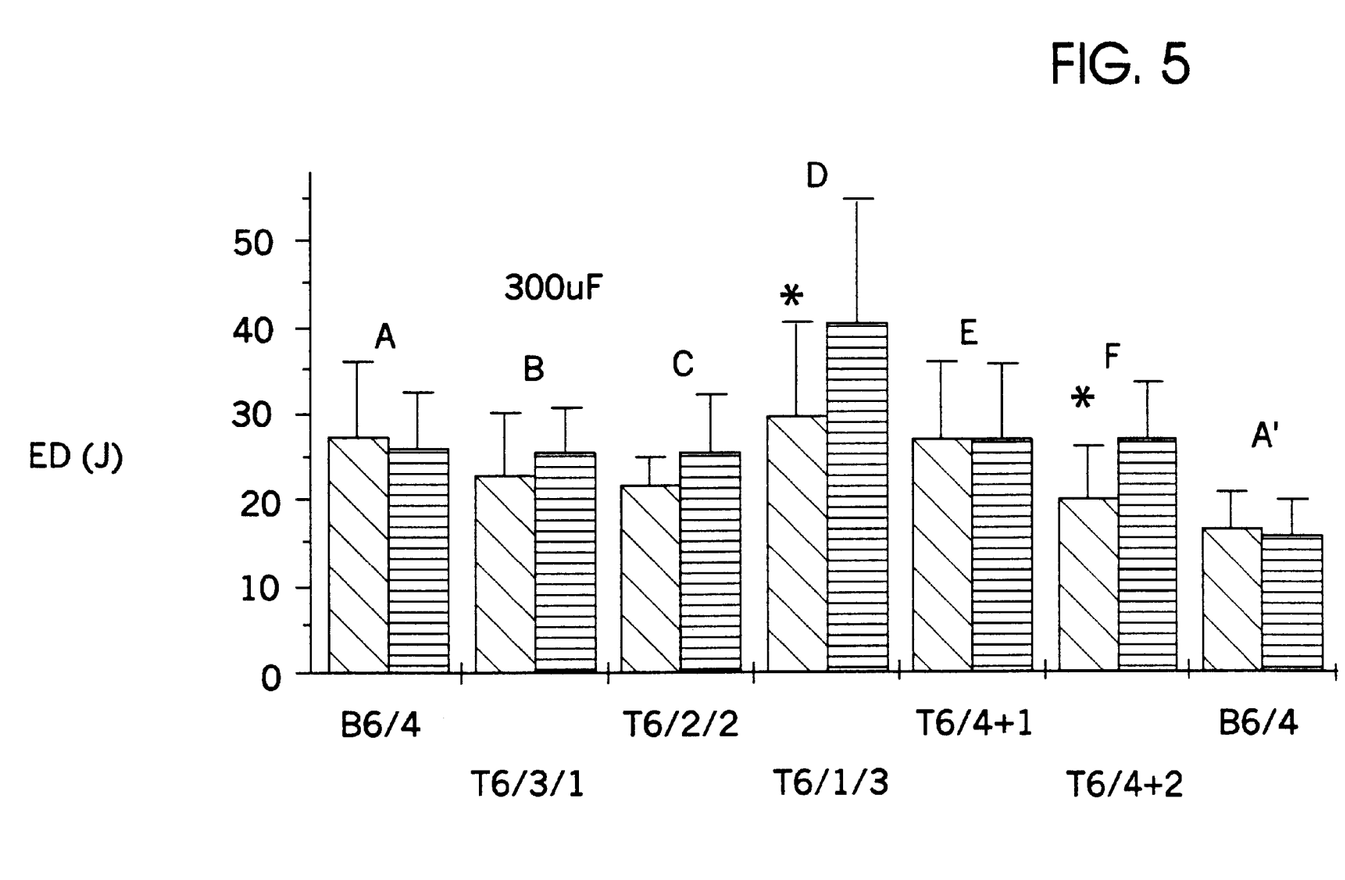
FIG. 5 illustrates experimental results in energy delivered (ED) at the defibrillation threshhold, as obtained with the waveforms of FIG. 4 (solid bars represent RV anode (+); shaded bars indicate RV cathode (−))
Figure 6:
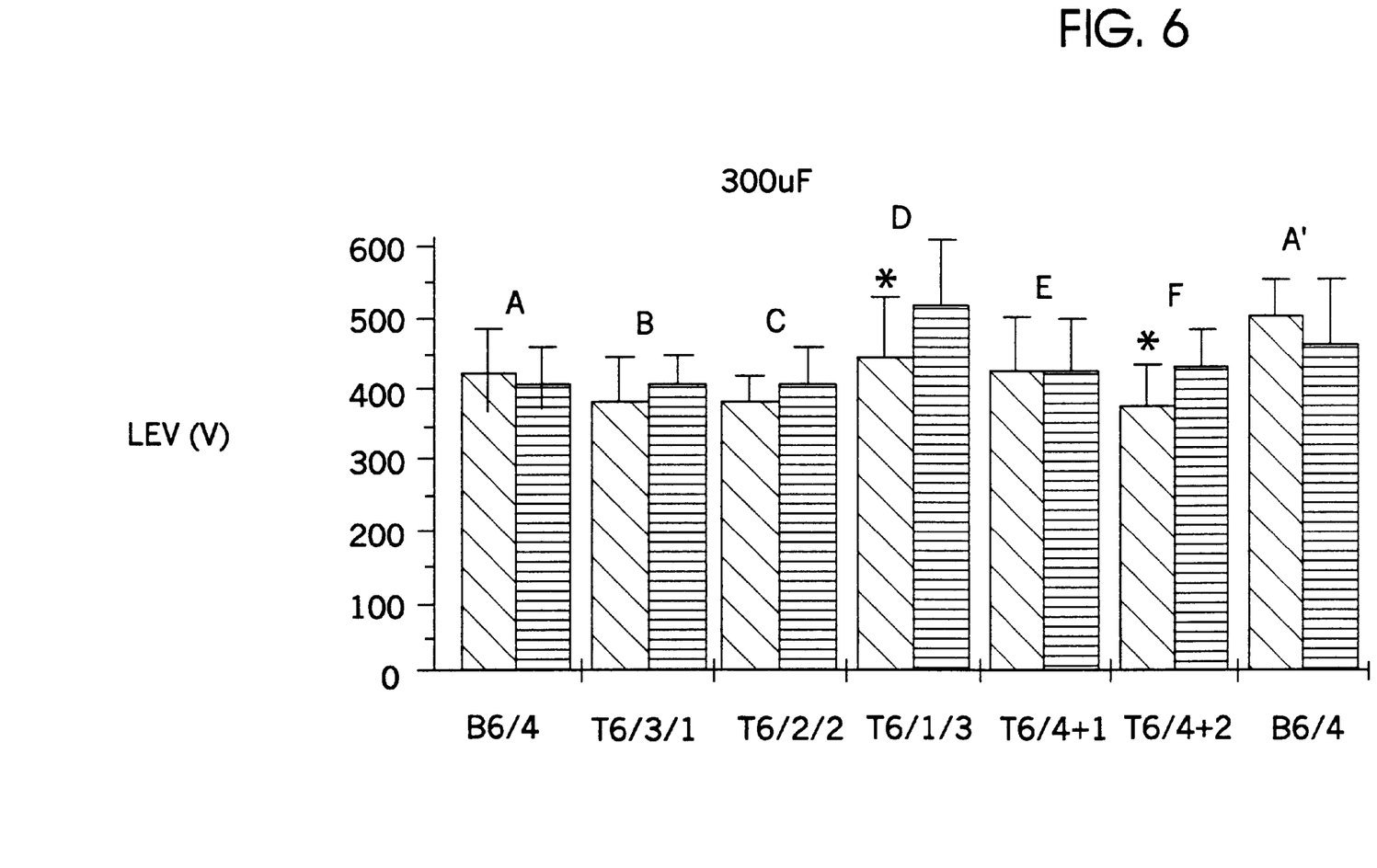
FIG. 6 illustrates experimental results in Leading Edge Voltage for the first phase (LEV), as obtained with the waveforms of FIG. 4.

Results are given in FIG. 5 and FIG. 6. Note the lower energy levels and lower voltages delivered for triphasic waveforms when the RV electrode is the anode.

EXAMPLE 2

Figure 7:
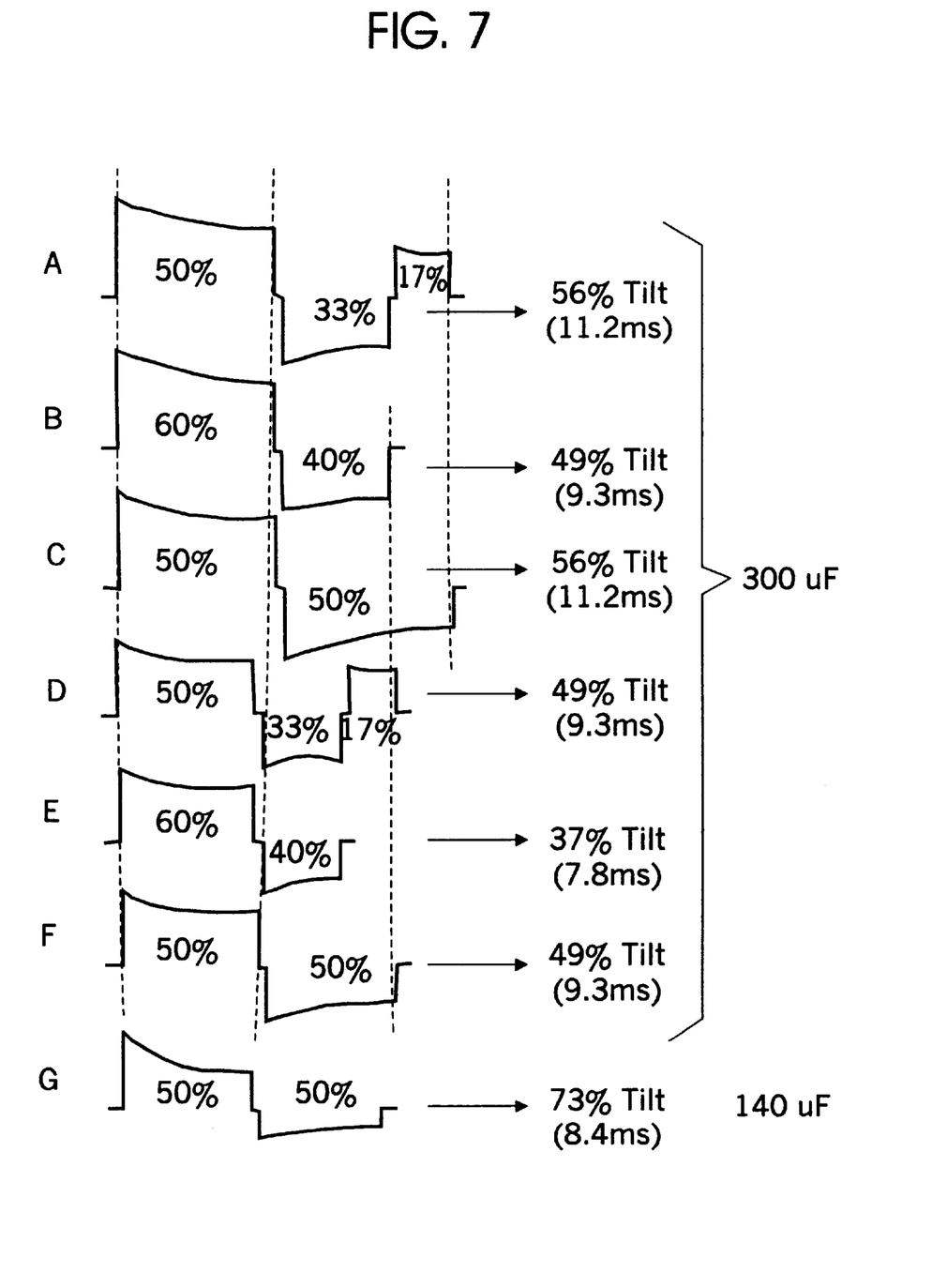
FIGS. 7A–7G illustrate additional triphasic waveforms of the present invention, along with several biphasic waveforms.

This example was carried out in essentially the same manner as described in Example 1 above, except that the waveforms schematically illustrated in FIG. 7 were used. Total times, percentage durations of each phase, and tilt is as given in connection with FIG. 4 above. The following electrode polarities were tested for each waveform:

1. The RV electrode cathode to the SVC and shell electrode anode (RV→SVC+Can);
2. The SVC and shell electrode cathode to the RV electrode anode (SVC+Can→Rv+).

Figure 8:
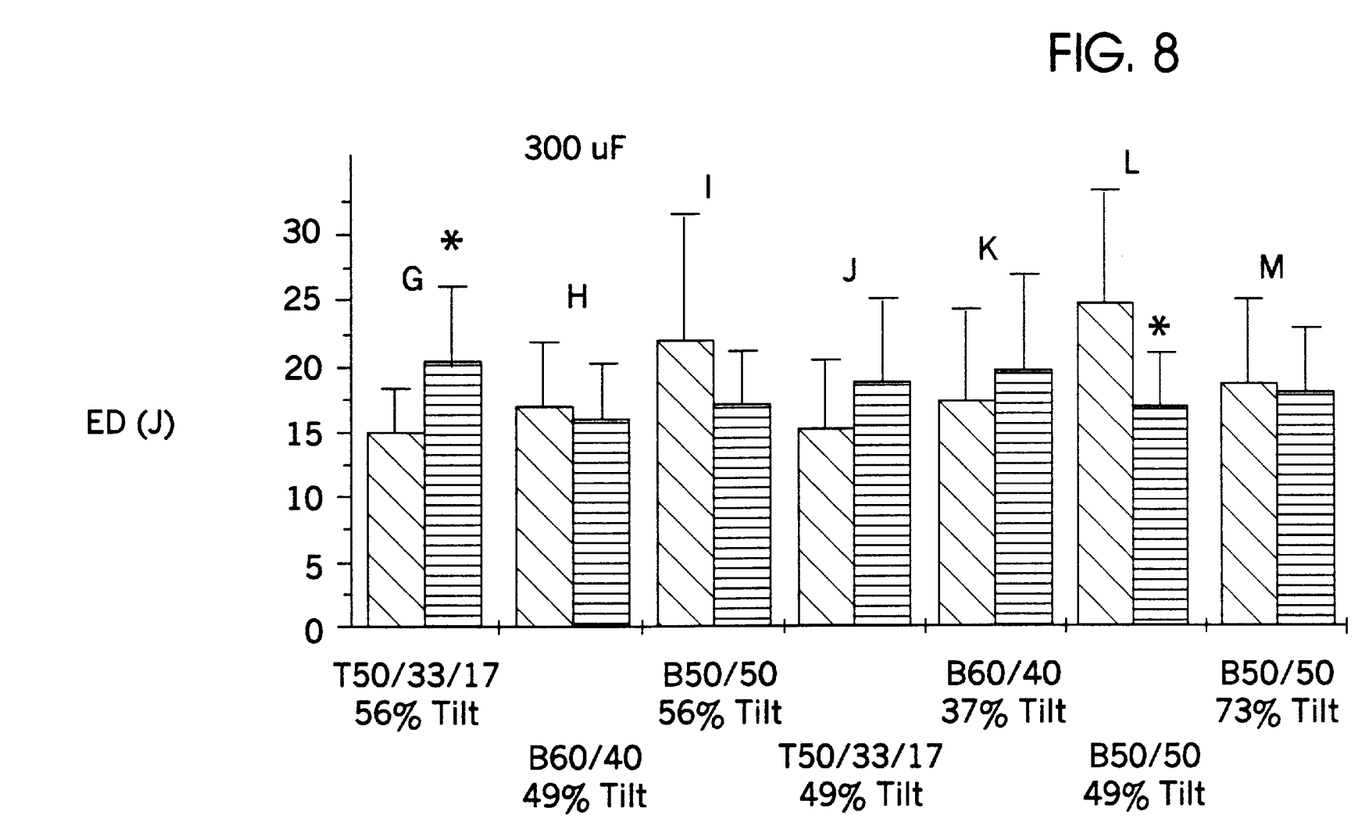
FIG. 8 illustrates experimental results obtained with the waveforms of FIG. 7.
Figure 9:
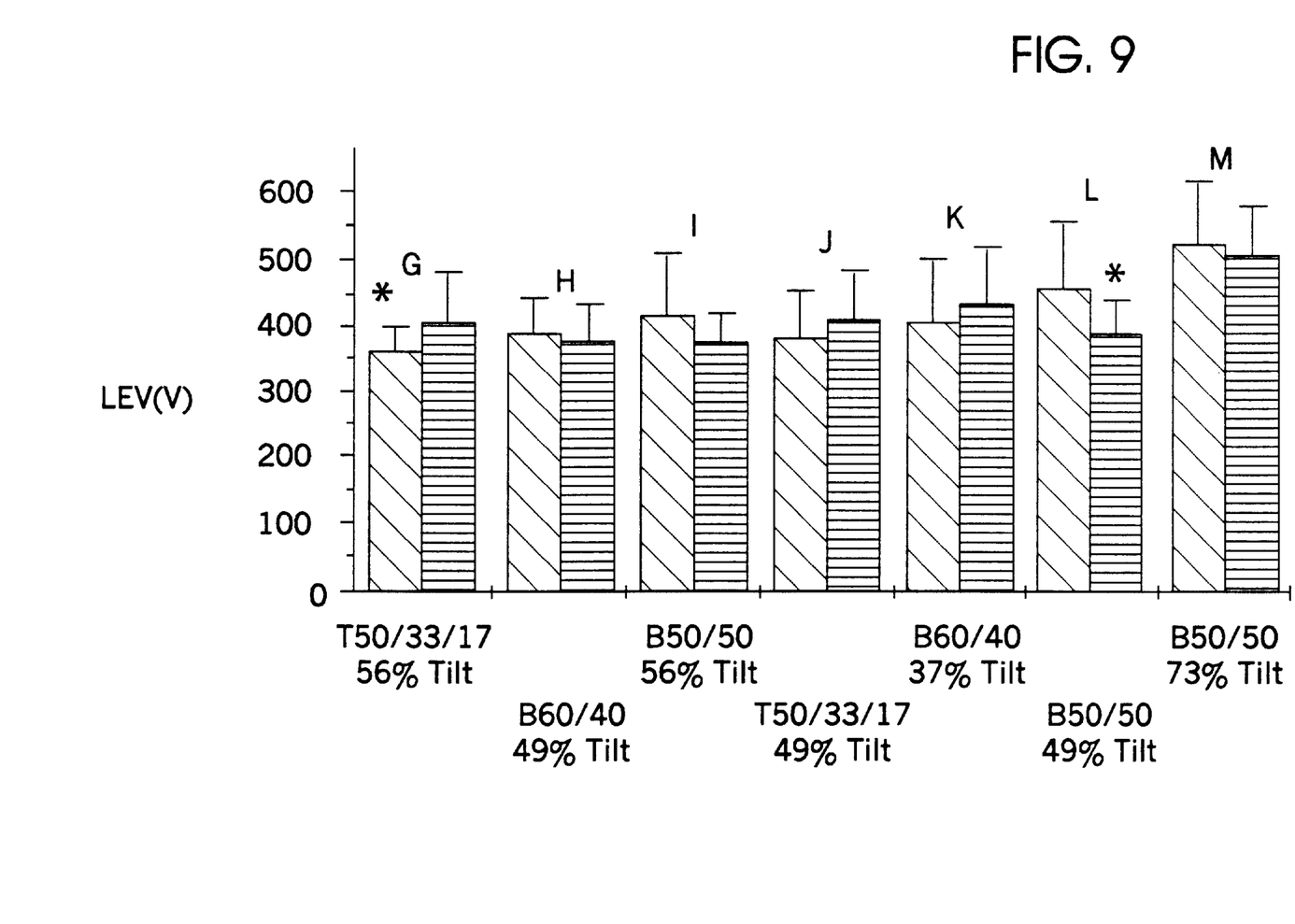
FIG. 9 illustrates experimental results obtained with the waveforms of FIG. 7.

Results are given in FIG. 8 and FIG. 9. Again, note the lower energy levels and lower voltages delivered for triphasic waveforms when the RV electrode is the anode.

The foregoing examples are illustrative of the present invention, and are not to be construed as limiting thereof. The invention is defined by the following claims, with equivalents of the claims to be included therein.

We claim:

1. An implantable system for the defibrillation or cardioversion of the heart of a patient in need of such treatment, said system comprising:

a plurality of electrodes configured for delivering a triphasic defibrillation pulse along a predetermined current pathway in said heart, said plurality of electrodes including a first electrode configured for positioning in the right ventricle of said heart;

a power supply; and a control circuit operatively associated with said electrodes and said power supply, said control circuit configured for delivering a triphasic defibrillation pulse through said electrodes;

said triphasic defibrillation pulse comprising a first phase, a second phase having a polarity opposite from said first phase, and a third phase having a polarity the same as said first phase;

with said control circuit configured so that said first electrode is an anode for said first phase and third phase of said triphasic defibrillation pulse;

with said plurality of electrodes including a second electrode configured for positioning in the superior vena cava of said patient and a third electrode configured for positioning in the left thoracic region of said patient;

and with said control circuit configured so that said second and third electrodes are cathodes for said first and third phases.

2. A system according to claim 1, said control circuit configured so that of said second and third phases have a combined duration not greater than the duration of said first phase.

3. A system according to claim 1, wherein said defibrillation pulse has an energy not more than about 40 Joules in strength.

4. A system according to claim 1, said control circuit configured so that:

said first phase is from 3 to 50 milliseconds in duration;

said second phase is from 2 to 15 milliseconds in duration; and said third phase is from one to 15 milliseconds in duration.

5. A system according to claim 1, said control circuit configured so that said defibrillation pulse has a tilt of at least 40%.

6. A system according to claim 1, said control circuit configured so that said defibrillation pulse has a tilt of at least 50%.

7. A system according to claim 1, wherein:

said defibrillation pulse is not more than about 35 Joules in strength;

said first phase is from 5 to 40 milliseconds in duration;

said second phase is from 6 to 12 milliseconds in duration; and said third phase is from 2 to 6 milliseconds in duration;

said control circuit configured so that said defibrillation pulse has a tilt of at least 50%.

8. A method for the defibrillation or cardioversion of the heart of a patient in need of such treatment, said method comprising:

positioning a plurality of electrodes for delivering a triphasic defibrillation pulse along a predetermined current pathway in said heart, said plurality of electrodes including a first electrode positioned in the right ventricle of said heart; and then delivering a triphasic defibrillation pulse through said electrodes, said triphasic defibrillation pulse comprising a first phase, a second phase having a polarity opposite from said first phase, and a third phase having a polarity the same as said first phase; wherein said first electrode is an anode for said first phase and third phase of said triphasic defibrillation pulse;

said plurality of electrodes including a second electrode positioned in the superior vena cava of said patient and a third electrode positioned in the left thoracic region of said patient;

with said second and third electrodes being cathodes for said first and third phases.

9. A method according to claim 8, wherein said delivery step involves delivering triphasic pulses whose durations of said second and third phases together are not greater than the duration of said first phase.

10. A method according to claim 8, wherein delivery step involves delivering a pulse not greater than about 40 Joules in strength.

11. A method according to claim 8, wherein said delivering step involves generating:

said first phase from 3 to 50 milliseconds in duration;

said second phase from 2 to 15 milliseconds in duration; and said third phase from one to 15 milliseconds in duration.

12. A method according to claim 8, wherein said delivering step involves delivering defibrillation pulse having a tilt of at least 80%.

* * * * *

UNITED STATES PATENT AND TRADEMARK OFFICE
CERTIFICATE OF CORRECTION

PATENT NO. : 6,002,962
DATED : December 14, 1999
INVENTOR(S) : Huang, et al.

It is certified that error appears in the above-identified patent and that said Letters Patent is hereby corrected as shown below:

In the Claims

Claim 10, column 8, line 37, should read:
-- 10. A method according to claim 8, wherein said delivery step --

Claim 12, column 8, line 47, should read:
-- ering step involves delivering a defibrillation pulse having a --

Signed and Sealed this

Twenty-ninth Day of May, 2001

Attest:

NICHOLAS P. GODICI

Attesting Officer

Acting Director of the United States Patent and Trademark Office